(12) United States Patent
Gregory et al.

(10) Patent No.: US 9,750,933 B2
(45) Date of Patent: Sep. 5, 2017

(54) TRANSCUTANEOUS NEURAL STIMULATION DEVICE

(71) Applicants: Daniel T. Gregory, Wilmington, FL (US); Roy A. Stimits, Wilmington, FL (US); Stephan D. Glenn, Wilmington, NC (US)

(72) Inventors: Daniel T. Gregory, Wilmington, FL (US); Roy A. Stimits, Wilmington, FL (US); Stephan D. Glenn, Wilmington, NC (US)

( * ) Notice: Subject to any disclaimer, the term of this patent is extended or adjusted under 35 U.S.C. 154(b) by 0 days.

(21) Appl. No.: 14/974,175

(22) Filed: Dec. 18, 2015

(65) Prior Publication Data
US 2016/0175585 A1  Jun. 23, 2016

Related U.S. Application Data

(60) Provisional application No. 62/094,011, filed on Dec. 18, 2014.

(51) Int. Cl.
*A61N 1/04* (2006.01)
*A61N 1/20* (2006.01)
*A61N 1/05* (2006.01)
*A61N 1/36* (2006.01)

(52) U.S. Cl.
CPC ............ *A61N 1/20* (2013.01); *A61N 1/0456* (2013.01); *A61N 1/0484* (2013.01); *A61N 1/0526* (2013.01); *A61N 1/0529* (2013.01); *A61N 1/36025* (2013.01)

(58) Field of Classification Search
CPC ...... A61N 1/20; A61N 1/0484; A61N 1/0456; A61N 1/0526; A61N 1/0531
See application file for complete search history.

(56) References Cited

U.S. PATENT DOCUMENTS

| | | | |
|---|---|---|---|
| 6,402,678 B1 | 6/2002 | Fischell | |
| 6,735,475 B1 | 5/2004 | Whitehurst | |
| 7,494,458 B2 | 2/2009 | Fiuschell | |
| 7,988,613 B2 | 8/2011 | Becker | |
| 8,239,030 B1 * | 8/2012 | Hagedorn | A61B 5/0482 607/45 |
| 8,262,556 B2 | 9/2012 | Fischell | |
| 8,428,734 B2 | 4/2013 | Rigaux | |
| 8,577,466 B2 | 11/2013 | Mashiach | |
| 8,676,324 B2 | 3/2014 | Simon | |
| 8,676,330 B2 | 3/2014 | Simon | |
| 8,909,344 B2 * | 12/2014 | Arle | A61N 1/0484 607/139 |
| 2013/0204315 A1 * | 8/2013 | Wongsarnpigoon | A61N 1/36021 607/45 |

* cited by examiner

*Primary Examiner* — Tammie K Heller
(74) *Attorney, Agent, or Firm* — Allen F. Bennett; Bennett Intellectual Property

(57) ABSTRACT

A non-invasive, transcutaneous electrical device stimulates nerves using unpulsed, constant direct current. The device uses a constant, unpulsed direct electric current of low constant voltage and power through air core uninsulated wire coil electrodes. The device includes a switch to open or close the circuit, a fuse that serves as the automatic overload trip voltage level, and two wire coil electrodes of uninsulated wire. The coil electrodes are positioned on the forehead directly superior to the eyes proximal to the supraorbital and supratrochlear nerves and apply a direct current transcutaneously to the forehead.

6 Claims, 5 Drawing Sheets

TRANSCUTANEOUS NEURAL STIMULATION DEVICE

CROSS-REFERENCE TO RELATED APPLICATIONS

This application claims priority to U.S. Provisional Application Ser. No. 62/094,011 filed on Dec. 18, 2014, the contents of which are hereby incorporated in their entirety.

STATEMENT REGARDING FEDERALLY SPONSORED RESEARCH OR DEVELOPMENT

Not Applicable.

NAMES OF PARTIES TO A JOINT RESEARCH AGREEMENT

Not Applicable

REFERENCE TO SEQUENCE LISTING, A TABLE, OR A COMPUTER PROGRAM LISTING APPENDIX SUBMITTED ON A COMPACT DISC AND INCORPORATION-BY-REFERENCE OF THE MATERIAL

Not Applicable.

COPYRIGHT NOTICE

Not Applicable

BACKGROUND OF THE INVENTION

Field of Endeavor

The present invention relates to systems and methods for generating a direct electric current transcutaneously. More particularly, the invention relates to a neural stimulation device for generating a constant, direct current at a supraorbital location to relieve headaches and other ailments.

Background Information

The roots of migraine attacks are believed by some clinicians and researchers to be self-propagating waves of cerebral neuronal firing, known as spreading depolarizations. Worldwide, primary headache disorders are the fifth leading cause of disability for women. The annual prevalence of migraine in the United States is 18% for adult women and the lifetime prevalence of migraine for women is estimated to be 26%.

A variety of different nerves may contribute to migraines or similar ailments. FIGS. 1 and 2 show many of the nerves of the face and scalp of a human head 10. The supraorbital nerve 12, the supratrochlear nerve 14, infratrochlear nerve 16, the external nasal nerve 18, and the lacrimal nerve 20 are located around and above the eyes. The zygomatico-temporal nerve 22, the infraorbital nerve 24 and the zygomatico-facial nerve 26 are generally located on the cheek and side of the face up to the temple. The auriculotemporal nerve 28, the buccal nerve 30, the mental nerve 32 and the great auricular nerve 34 are located along the chin and extending to the ear. The greater occipital nerve 36 and lesser occipital nerve 38 are located near the rear of the head.

Devices have been developed to treat or prevent migraine headaches, pain, and other neurological disorders using a number of approaches. One approach using implanted electrodes (invasive devices) has been used with neurostimulation devices that deliver pulses of electrical current directly to targeted nerves. There are numerous reports using neurostimulation of the occipital nerves, supraorbital, and/or infraorbital nerves using implanted electrodes (especially located at the back of the head above the neck) for treatment of migraine headaches and craniofacial pain. However, a significant number of patients suffer side effects from the implanted electrodes. Many patients treated with implanted electrodes also suffer from lack of efficacy of these devices. Either the side effects or lack of efficacy often result in the removal or replacement of the electrodes. In one report 5 of 22 patients (22.7%) with a device with electrodes implanted to treat craniofacial pain had the device removed with a mean duration of follow-up of 35 months. The reasons for removal of the device were: two patients (9.1%) had the device removed because of pain improvement over time, two patients (9.1%) had the device removed due to loss of effectiveness, and one patient (4.6%) had the device removed due to late infection. The remainder of the patients enjoyed either complete (15 patients, 68.2%) or partial (two patients, 9.1%) pain relief. Three patients (13.6%) underwent repeated operations due to lead erosion, infection or electrode migration.

There are reports of the neurostimulation of the occipital nerves, supraorbital and/or infraorbital nerves with implanted electrodes (posterior head superior to the neck) for treatment of migraine headaches and craniofacial pain. In a randomized, controlled multicenter study of patients diagnosed with chronic migraine, patients were implanted with a neurostimulation device near the occipital nerves and then randomized 2:1. The primary endpoint of this study was the percentage of responders (defined as patients that achieved a ≥50% reduction in mean daily visual analog scale scores) in each group at 12 weeks. The authors reported that there was no significant difference in the percentage of responders in patients with the Active device when compared with the Control device (95% lower confidence boundary of −0.06; p=0.55). However, when the results of the sham-treated patients were compared with the Active device treated patients, there were statistically significant reductions in secondary endpoints: number of headache days (Active device 6.1 decreased headache days from a baseline of 22.4 headache days versus Control device decreased 3.0 headache days 3.0 from a baseline of 20.1 headache days; p=0.008). Also, decreased by the Active treatment versus Control were migraine-related disability (p=0.001) and direct reports of pain relief (p=0.001). The most common adverse event reported in the study was persistent implant site pain.

In U.S. Pat. No. 6,735,475 to Whitehurst et al. discloses a fully implantable miniature neurostimulator for stimulation as a therapy for headache and/or facial pain. U.S. Pat. No. 8,577,466 to Mashiach et al. describes a device configured for implantation into a body of a subject that may include an antenna configured to receive a signal. The implantable device may also include at least one pair of modulation electrodes configured to be implanted into the body of the subject in the vicinity of at least one nerve to be modulated. In this device at least one pair of modulation electrodes is configured to receive an applied electric signal. In response to the signal received by the antenna an electrical field modulates at least one nerve from a position where at least one pair of modulation electrodes does not contact at least one nerve.

Sphenopalatine interventions (ablations or nerve stimulation) have been used for over 100 years to treat migraine headaches. Another implantable device is a sphenopalatine ganglion neurostimulator that is implanted through an oral incision and placed along the maxilla. This device can apply on-demand sphenopalatine ganglion stimulation for the treatment of severe primary headache. However, invasive neurostimulator devices to ameliorate migraines remain unpopular with most migraine patients, largely due to lack of efficacy and post-surgical complications.

In one example, two patients had the devices removed because of pain improvement over time; in three patients the devices were removed due to loss of effectiveness (two cases) or late infection (one). The rest are enjoying either complete (15 patients) or partial (two patients) pain relief. Three patients underwent repeated operations due to lead erosion, infection or migration. Patients were implanted with a neurostimulation device near the occipital nerves and randomized 2:1 into a randomized, controlled multicenter study of patients diagnosed with chronic migraine. The primary endpoint was a difference in the percentage of responders (defined as patients that achieved a ≥50% reduction in mean daily visual analog scale scores) in each group at 12 weeks. They observed no significant difference in the percentage of responders in the Active compared with the Control group (95% lower confidence bound (LCB) of −0.06; p=0.55). However, there was a significant reduction in the number of headache days (Active Group median reduction of 6.1 days from a baseline of 22.4 days versus Control Group median reduction of 3.0 days from a baseline of 20.1 days; p=0.008). Also reported were migraine-related disability decreased (p=0.001) and direct reports of pain relief decreased (p=0.001). The most common adverse event reported in the study was persistent implant site pain.

Application of modulating electric signals via implanted electrodes attached directly to the nerves to be stimulated—either to one or both of a patient's trigeminal and glossopharyngeal nerves may treat, control or prevent of medical, psychiatric or neurological disorders; examples include: voluntary and involuntary disorders; migraine; epileptic seizure; motor disorders; Parkinson's disease; cerebral palsy; spasticity; chronic nervous illnesses and involuntary movement; pancreatic endocrine disorders including diabetes and hypoglycemia; dementia including cortical, subcortical, multi-infarct, Alzheimer's disease; Pick's disease; sleep disorders including central sleep apnea, insomnia and hypersomnia; eating disorders including anorexia nervosa, bulimia and compulsive overeating; and neuropsychiatric disorders including schizophrenia, depression and borderline personality disorder (See U.S. Pat. No. 5,540,734).

U.S. Pat. No. 6,954,668 describes an apparatus for intraoral stimulation of the trigeminal nerve includes an energy source that imparts energy to a tooth to stimulate the trigeminal nerve and an attachment portion to secure the energy source in a mouth in proximity to the tooth. This stimulation has been experimentally shown to induce and/or enhance relaxation and/or sleep.

Invasive stimulation of the occipital nerve has been used to reduce migraine headaches in migraine patients. Complete diary data were available for 66 of the 75 patients. Responders achieved at least a 50% reduction in the number of headache days per month or a three-point or greater reduction in average overall pain intensity compared with baseline. The three-month responder rates were 39% for AS, 6% for PS and 0% for MM. No unanticipated adverse device events occurred.

The effect of pulsed electromagnetic fields on migraine activity has been evaluated in a double-blind, placebo-controlled study of 42 subjects (34 women and 8 men), who were selected to meet the International Headache Society's migraine criteria. Subjects kept a one month, pretreatment, baseline log of headache activity prior to being randomized to having either actual or placebo pulsing electromagnetic fields applied to their inner thighs for one hour per day, five days per week for two weeks. After exposure, all subjects kept the log for at least one month of follow-up. During the first month of follow-up, 73% of subjects receiving actual exposure reported decreased headaches (45% "good decrease," 14% "excellent decrease" in headache activity) compared to half of those receiving the placebo (15% worse, 20% good, 0% excellent decrease in headache activity). Ten of the 22 subjects who had actual exposure received two additional weeks of actual exposure after their initial one month follow-up. All showed decreased headache activity (50% good, 38% excellent). Thirteen subjects from the actual exposure group elected not to receive additional exposure. Twelve of them showed decreased headache activity by the second month (29% good, 43% excellent decrease in headache activity). Eight of the subjects in the placebo group elected to receive two weeks of actual exposure after the initial one month follow-up with 75% showing decreased headache activity (38% good and 38% excellent decrease in headache activity). In conclusion, exposure of the inner thighs to pulsing electromagnetic fields for at least three weeks appears to be an effective, short-term intervention for migraine, but not tension headaches.

A non-invasive transcranial magnetic stimulator device for headache (Neuralieve) has been approved for marketing by the US Food and Drug Administration. This device described by Fischell et al. delivers brief duration, rapidly alternating, or pulsed, magnetic fields that are externally directed at spatially discrete regions of the brain to induce electrical currents for the treatment of headache.

U.S. Pat. No. 7,494,458 to Fischell et al. discloses an electromagnetic device that employs is a self-contained, battery operated, readily portable and easy-to-operate head-mounted magnetic depolarizer to generate a transient or time-varying high-intensity magnetic field. The magnetic field is directed into and around the user's head or neck to depolarize the neurons of the brain and/or the trigeminal nerve creating neuronal depolarization and terminate migraine or other types of headaches.

U.S. Pat. No. 6,402,678 to Fischell et al. discloses a device and method for treatment of migraine headaches using an intense magnetic field onto a region of the brain. An electrical current can be generated in the cerebral cortex that can depolarize a band of excited brain neurons that are a precursor to a migraine headache. The device can be positioned using headgear such as a bicycle helmet to direct the magnetic field at the correct part of the brain.

U.S. Pat. No. 8,262,556 to Fischell et al. discloses a means and methods for treatment of migraines and other disorders by application of intense magnetic pulses. They report stopping or decreasing the severity of migraine headaches using this magnetic pulser system.

The efficacy and safety of the Neuralieve device was tested in a randomized, double-blind, parallel-group, two-phase, sham-controlled study at 18 centers. A total of 267 adult patients (18-68 years of age) were enrolled in part 1 of the study. All individuals met the international criteria for migraine with aura, with visual aura preceding at least 30% of migraines followed by moderate or severe headache in more than 90% of those attacks. Sixty-six patients dropped out during part 1 of the study. For part 2 of the study, 201 patients were randomly allocated to either sham stimulation (n=99) or transcranial magnetic stimulation (n=102). Participants were instructed to treat up to three attacks over 3 months while experiencing aura. The primary outcome was pain-free response 2 hours after the first attack, and co-primary outcomes were non-inferiority at 2 hours for nausea, photophobia, and phonophobia.

Thirty-seven (37) patients failed to treat a migraine attack and were excluded from outcome analyses; 164 patients treated at least one attack with transcranial magnetic stimulation (n=82) or sham stimulation (n=82; modified intention-to-treat analysis set). Pain-free response rates after 2 hours were significantly higher with transcranial magnetic stimulation (32/82 [39%]) than with sham stimulation (18/82 [22%]), for a therapeutic gain of 17% (95% CI 3-31%; p=0·0179). Sustained pain-free response rates significantly favored transmagnetic stimulation at 24 hours and 48 hours post-treatment. Non-inferiority was shown for nausea, photophobia and phonophobia. No device-related serious adverse events were recorded, and the incidence and severity of adverse events were similar between transmagnetic stimulation and sham groups.

U.S. Pat. No. 8,428,734 to Rigaux et al. discloses a non-invasive transcutaneous electrical nerve stimulation (TENS) device (Cefaly device) has an electrical circuit that includes a programmable signal generator that produces pulses of electricity of between 150 and 450 microseconds duration with a maximum increase in intensity of 0 to 20 milliamperes at a rate of less than or equal to 40 microamperes per second and with a step up in intensity not exceeding 50 microamperes to stimulate the afferent paths of the supratrochlear and supraorbital nerves of the ophthalmic branch of the trigeminal nerve to prevent tension headaches or migraines.

However, the application of electrodes and significant electrical current to the forehead may produce extreme pain. The level of current applied, and thus tissue penetration, by this device is limited by the local pain and irritation associated with increased electrical current. Electrical stimulation devices are therefore of generally limited efficacy and acceptability for treatment of migraine and other primary headaches.

A double-blinded, randomized, sham-controlled trial testing the Cefaly device for control of migraine headaches was conducted at five Belgian tertiary headache clinics. Following a one month run-in, those patients with at least two migraine attacks per month were randomized at a 1:1 ratio to Cefaly or sham treatment. The Cefaly or sham treatment was applied daily for 20 minutes for a period of three months. The primary outcome measures for this study were the change in migraine days per month and the rate of 50% or greater responders. Sixty-seven patients were randomized and included in the intention-to-treat analysis. Between the run-in and third month of treatment, the mean number of migraine days decreased significantly in the Cefaly treatment group (6.94 versus 4.88; p=0.023), but not in the sham group (6.54 versus 6.22; p=0.608). The 50% or responder rate was significantly greater (p=0.023) in the Cefaly treatment group (38.1%) than in the sham group (12.1%). The number of monthly migraine attacks (p=0.044), the monthly headache days (p=0.041), and the monthly acute antimigraine drug intake (p=0.007) were also significantly reduced in the Cefaly treatment group but not in the sham group. There were no adverse events reported in either the Cefaly or the sham treatment groups.

U.S. Pat. No. 7,988,613 to Becker discloses an apparatus for generating frequencies of pulsed direct current signals that are related to sleep and alert states. This device is comprised of a circuit configured to produce a pulsed direct current signal having a frequency wherein the frequency falls within a range of brain wave frequencies. The device is capable of producing corresponding segments of pulsed direct current including a delta segment, a theta segment, an alpha segment and a beta segment. Each of the delta, theta, alpha and beta segments to a respective subrange of the brain wave frequencies. A frequency controller, coupled to the circuit, is configured to change the frequency of the pulsed direct current signal from a first frequency to a second frequency, wherein the second frequency is within a second one of the plurality of segments, and wherein the first frequency is a non-zero frequency outside of the second one of the plurality of segments. An inductor coil, coupled to the output of the circuit, is configured to generate a magnetic field from the pulsed direct current signal.

U.S. Pat. Nos. 8,676,324 and 8,676,330 to Simon et al. disclose non-invasive transcutaneous electrical nerve stimulation devices and magnetic stimulation devices. Methods of treating medical disorders using the energy delivered by these devices including migraine and other primary headaches such as cluster headaches, including nasal or paranasal sinus symptoms that resemble an immune-mediated response ("sinus" headaches). These disclosed methods may also be used to treat other disorders that may be co-morbid with migraine headaches, such as anxiety disorders. The disclosed methods may be used to stimulate one or both of the patient's vagus nerves or parts of the sympathetic nervous system and/or the adrenal glands.

In view of the foregoing, there is a need to provide an effective, painless, inexpensive apparatus for treating headaches, aura and other ailments for the large population of afflicted individuals who do not desire or could otherwise not afford pharmacologic or electromagnetic treatments.

It is also desirable to provide an apparatus and method for treating headaches, aura and similar pain using an effective and non-invasive procedure.

BRIEF SUMMARY OF THE INVENTION

Accordingly, the primary object of the present invention is to provide an apparatus and method for generating direct current to treat headaches, aura and similar pain. In addition, it is also an object of the invention to provide an apparatus and method for generating a direct current in a patient using a non-invasive apparatus.

In greater detail, a device in accordance with the principles of the invention includes wire coils acting as inductors to transcutaneously generate a direct current at the region of a headache or similar pain.

In one embodiment, a device in accordance with the principles of the invention generates no quantifiable electromagnetic field when direct electric current of the preferred configuration is allowed to flow through the electrode coils, as measured using a scalar gaussmeter with a linear Hall effect sensor (sensitivity 5 mv/G). No pulses or spikes of voltage or electrical current were measured in the device during its operation.

In another embodiment a portable battery powered electrical device passes a constant voltage direct electric current through two coils of wire. This device is powered by a standard 9 volt battery.

The preferred configuration of the electronic circuit reduces the voltage at the coils of uninsulated wire (electrode) to a preferred constant 3.2 volts. The output wire has one or more coils of uninsulated wire as electrodes each composed of two or three loops of unshielded wire that resembles a small eyeglasses frame.

It is therefore an object of the present invention to provide a neural stimulation device that transcutaneously induces a direct current adjacent to the supratrochlear and superorbital nerves of the forehead.

These and other objects and advantages of the present invention will become apparent from a reading of the attached specification and appended claims. There has thus been outlined, rather broadly, the more important features of the invention in order that the detailed description thereof that follows may be better understood, and in order that the present contribution to the art may be better appreciated. There are features of the invention that will be described hereinafter and which will form the subject matter of the claims appended hereto.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION

Figures 1, 2:
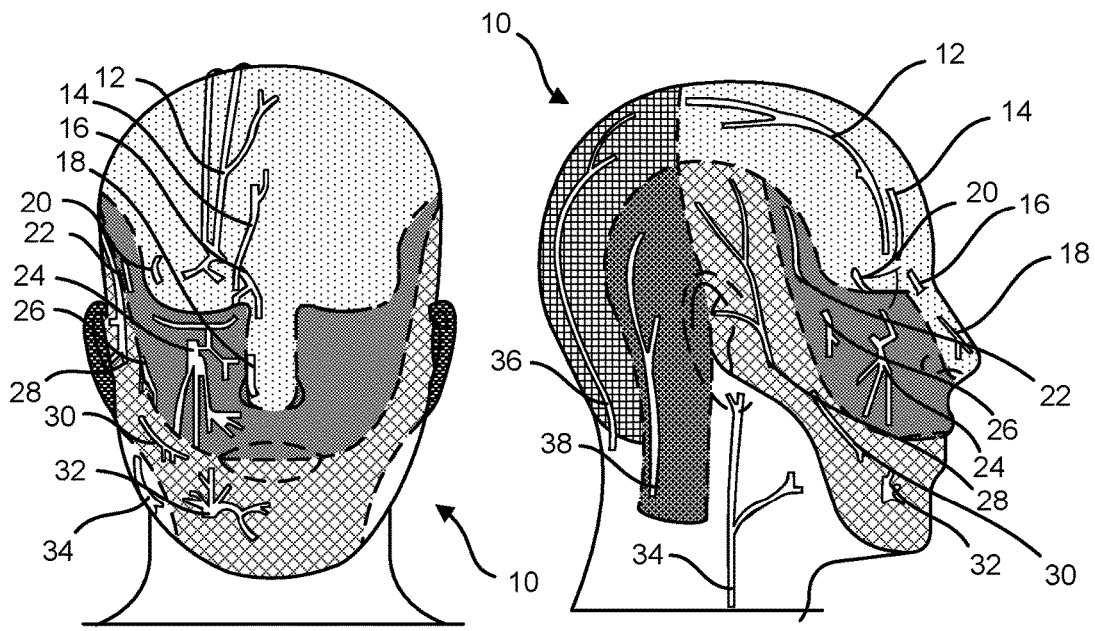
FIG. 1 is a front diagram of the nerves of a human head.
FIG. 2 is a side diagram of the nerves of a human head.

Before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

The invention provides a non-invasive, transcutaneous electrical device that may stimulate nerves using unpulsed, constant direct current. The device may have an electronic circuit that produces a unpulsed, constant direct electric current of constant voltage and power in the range of 2.6 to 8.4 volts and one embodiment may provide a current of approximately 3.2 volts. The current may have 54 to 142.5 mW power, and in one embodiment may have approximately 114 mW through air core uninsulated wire coils as electrodes. The device may be powered by a direct current source, e.g. batteries or a transformer that produces constant voltage direct current. The configuration of the electronic circuit may reduce the voltage at the coils of uninsulated wire (electrode) to approximately 3.2 volts. The output wire may have two coils of uninsulated wire as electrodes, each composed of two or more loops of unshielded wire that resemble a small eyeglasses frame.

Figure 3:
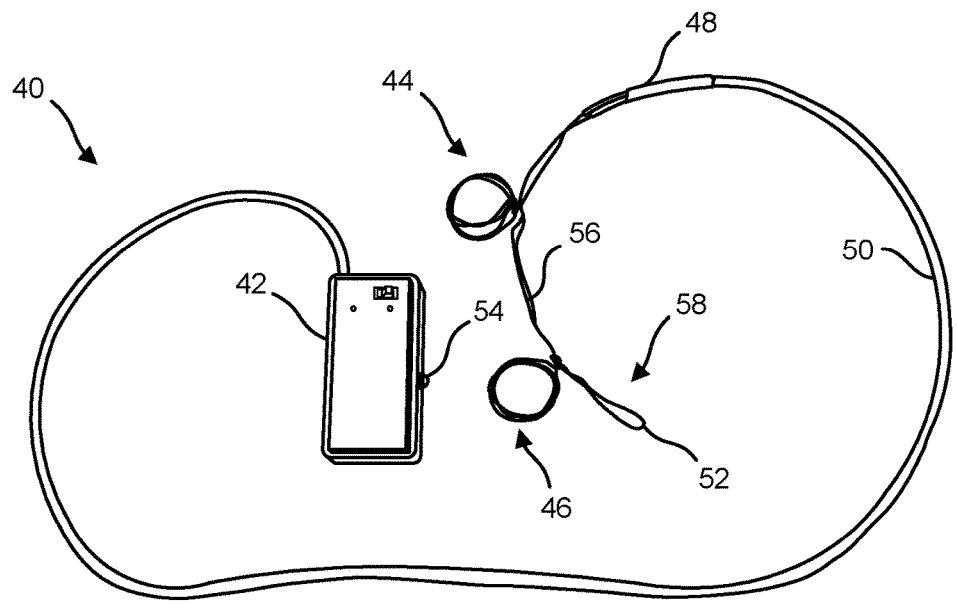
FIG. 3 is a perspective view of a transcutaneous neural stimulation device in accordance with the principles of the invention.

FIG. 3 shows an electrical current exposure device 40 in accordance with the principles of the invention. The electrical current exposure device 40 may have a power source 42 and two exposure coils 44 and 46. The two exposure coils 44 and 46 may be electrically connected to the power source 42 by wire 48. The wire 48 may be at least partially covered by a jacket 50. The jacket 50 may be plastic, rubber or any other material suitable for acting as a jacket for electrical wiring. The wire 48 may be insulated. The coils 44 and 46 may be comprised of portions of the wire 48 that may or may not be insulated. In this embodiment, the wire 48 may be formed from a single wire that has been folded at a kink 52 to form two parallel wires.

The power source 42 may supply a direct current that runs through wire 48. The power source 42 may have an internal power supply such as for example a battery and may include means for regulating the current traveling through the wire 48. In this embodiment, the power source 42 includes an LED indicator light 54. In use, the coils 44 and 46 may be placed directly on the skin over one or more nerves in order to expose the nerves to an external direct current.

The coils 44 and 46 of the electrical current exposure device 40 may each be formed from one or more loops formed by the wire 48. Optionally, a circular frame may be used to form the coils by wrapping loops of the wire 48 about the frame. The loops may be connected by a bridge wire 56. The electrical current exposure device may also optionally include a distal arm region 58 extending from the second coil 46 in a direction opposite to the bridge wire 56 and the first coil 44. The electric current exposure device 40 may also optionally have a support device, such as a headband, incorporated into it to hold the coils 44 and 46 in a desired position, such as on the forehead above the eyes.

Figure 4:
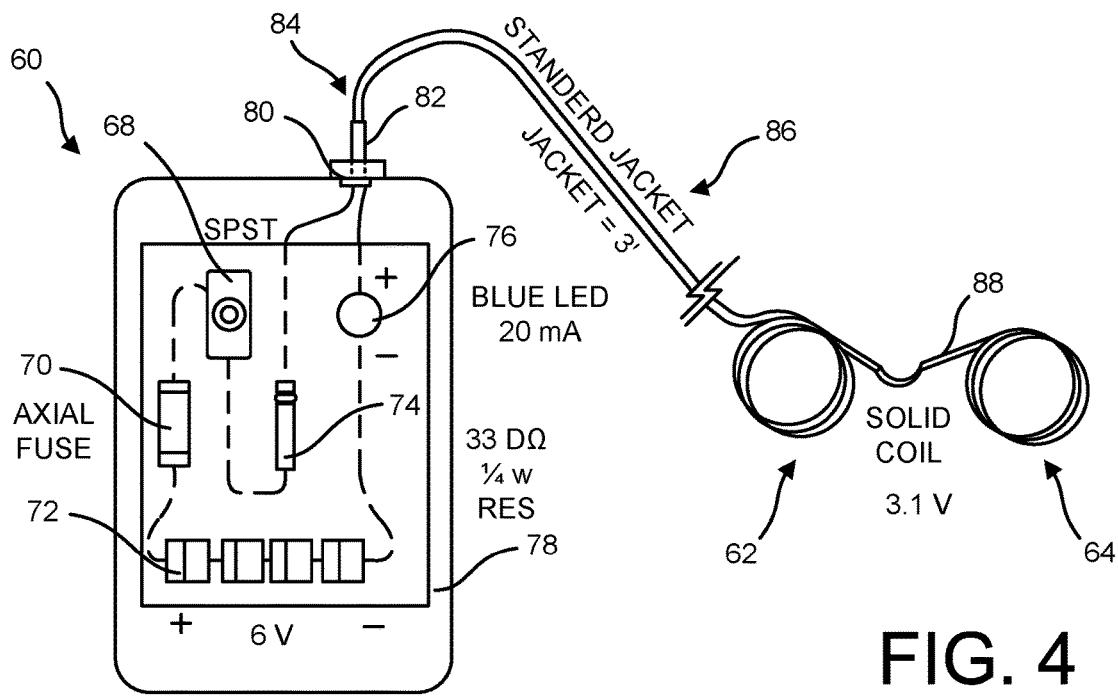
FIG. 4 is a diagram of a 6 volt transcutaneous neural stimulation device in accordance with the principles of the invention.

FIG. 4 shows a diagram of the internal mechanisms of a power source 60 and two exposure coils 62 and 64 in accordance with the principles of the invention. The power source 60 may include a switch 68 to open and close the circuit (i.e. turn the device on or off), a fuse 70 that serves as the automatic overload trip, a direct current power supply 72, a resister 74, and an LED 76 for indicating when the device is "on" and operating. In this embodiment, the resister 74 is positioned between the switch 68 and the socket 80. The components of the power source 60 may be contained within a body 78.

A socket 80 may receive a removable direct current jack connected to a plug 82 on the proximal end 84 of electrical wiring 86 that may supply electrical current to the exposure coils 62 and 64. The exposure coils 62 and 64 may each be comprised of one or more loops of electrically conductive wire and may be connected by means of a bridge wire 88.

Figure 5:
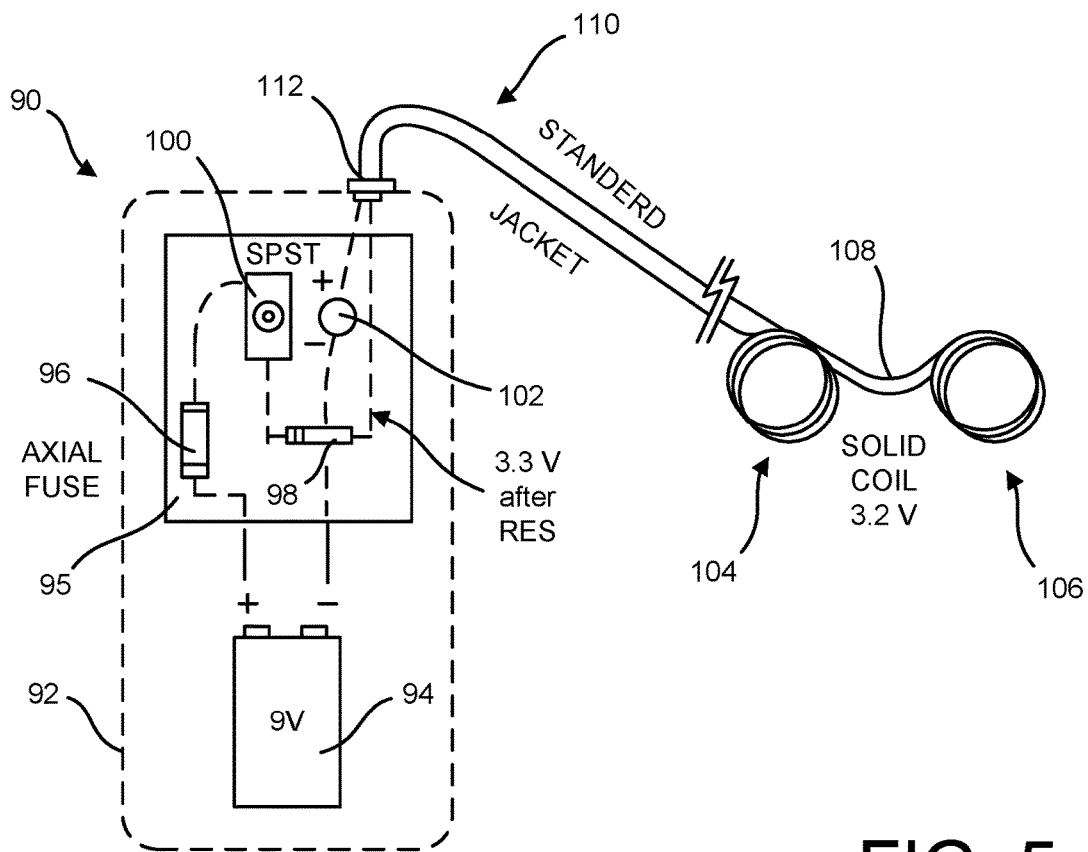
FIG. 5 is a diagram of 9 volt alternative embodiment of a transcutaneous neural stimulation device in accordance with the principles of the invention.

FIG. 5 shows an alternative embodiment of a power source 90. In this embodiment, a housing 92 contains the power supply 94, which in this case is a 9 volt battery. A circuit board 95 may include a fuse 96 electrically positioned between the power supply 94 and the switch 100. A resistor 98 may regulate the current supplied by the power source 90. An LED light may indicate when the power source is turned on. As with other embodiments, the two exposure coils 104 and 106 may be electrically connected by a bridge wire 108 that may be rigid enough to hold the exposure coils 104 and 106 a suitable distance from each other such that they made each rest above an eye on a person's forehead. The two exposure coils 104 and 106 may be electrically connected to the power source 90 by a power cord 110. The proximal end of the power cord 110 may be connected by a jack 113 (((need to add on drawing))) to a socket 112 located on the housing 92.

Figure 6:
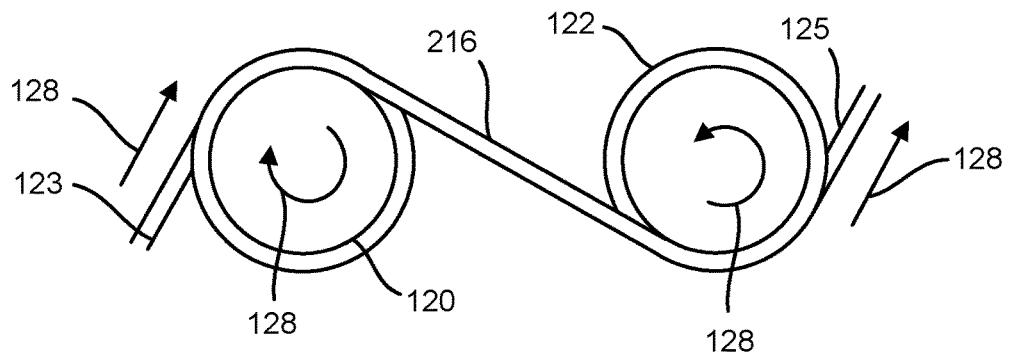
FIG. 6 is a front elevational view of an alternative coil embodiment of a transcutaneous neural stimulation device in accordance with the principles of the invention.
Figure 7:
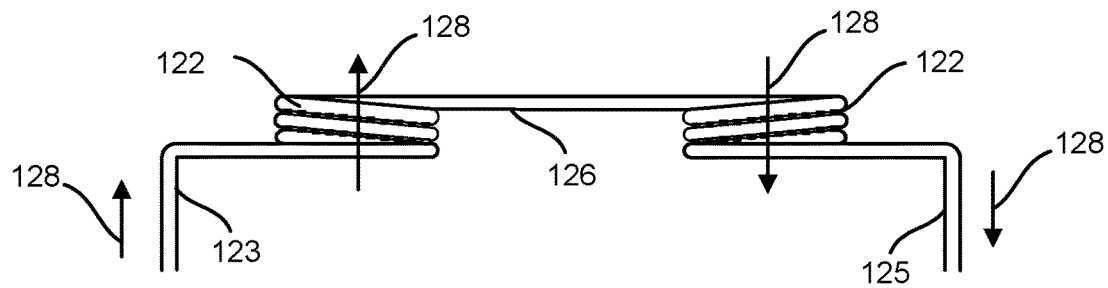
FIG. 7 is a top plan view of an alternative coil embodiment of a transcutaneous neural stimulation device in accordance with the principles of the invention.

FIGS. 6 and 7 show an alternative configuration for two exposure coils 120 and 122. In this embodiment, the bridge wire 126 and the coils 120 and 122 have been configured such that the direct current in the coils 120 and 122 flow in opposite directions, as indicated by current flow arrows 128. A direct current may enter the coils through electrical wire 123 and exit the coils through electrical wire 125. This configuration may apply inverse direct current to neighboring locations. It may be desirable to use such a configuration for exposing nerves to direct current in different situations.

Figure 8:
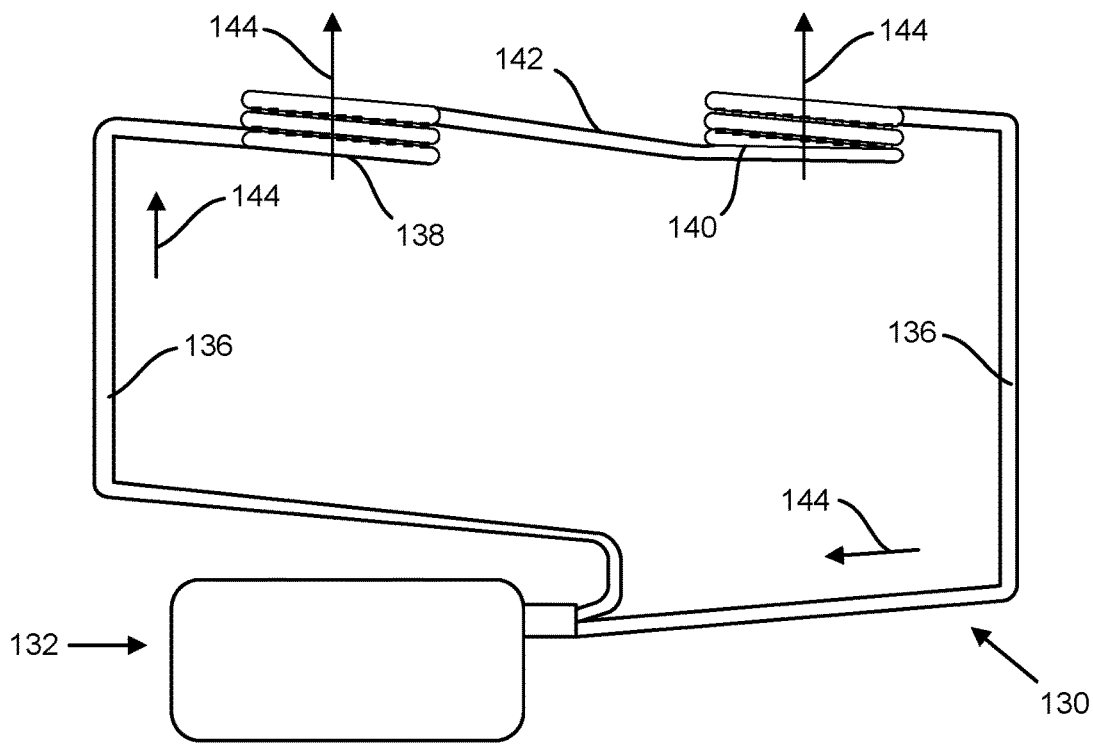
FIG. 8 is a top plan view of an alternative embodiment of a transcutaneous neural stimulation device in accordance with the principles of the invention.

FIG. 8 shows another alternative embodiment for an electrical current exposure device 130. The device 130 may include a power source 132 similar to those described above. Electrical wires 134 and 136 supply a direct current through the exposure coils 138 and 140. Due to the arrangements of the coils 138 and 140 and the bridge wire 142 connecting the two coils, the current flows in the same circular direction through each coil as indicated by arrows 144.

Figure 9:
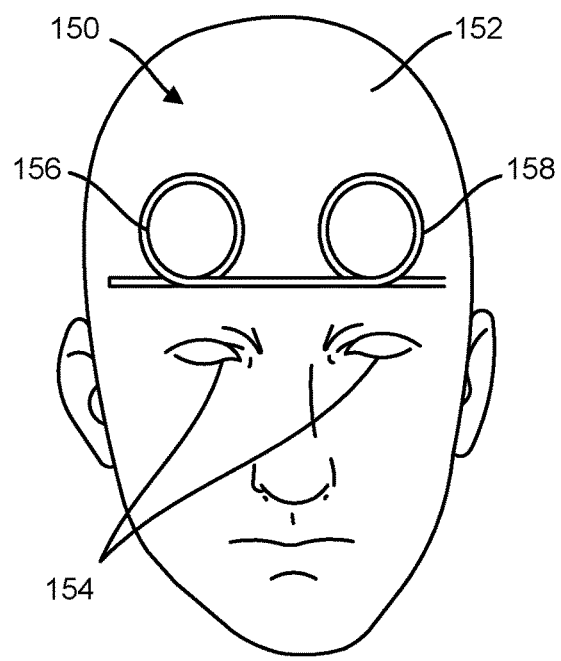
FIG. 9 is a frontal perspective of coil emplacement over the forehead.
Figure 10:
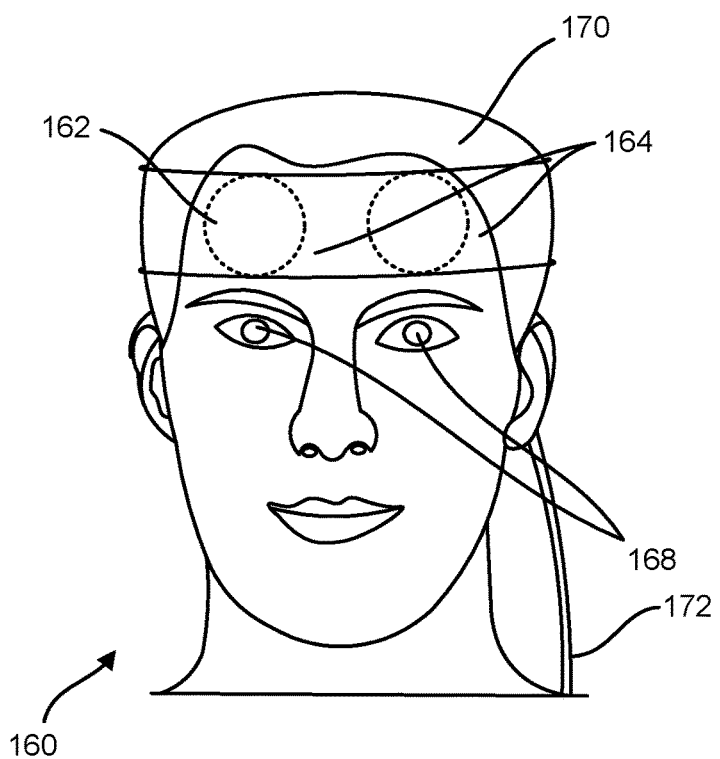
FIG. 10 is a front's environmental view of a person wearing a transcutaneous neural stimulation device in accordance with the principles of the invention.

FIG. 9 shows an alternative embodiment of an electric current exposure device 150 positioned on a person's head 152 above the eyes 154. In this configuration, the exposure coils 156 and 158 are placed approximately above the supraorbital nerves on the forehead. FIG. 10 shows another alternative embodiment of an electric current exposure device 160. The electric current exposure device 160 includes a headband 162 supporting two exposure coils 164 above the eyes 168 of a person's head 170. Electric wiring 172 provides electrical connection to a power source, not shown.

Without being bound by theory, it is believed that the electric field generated by the exposure coils may induce a direct current transcutaneously above the supraorbital and supratrochlear c nerves in a direction contrary to the current flowing through the coils. This direct current, when applied transcutaneously in this manner through the skin and tissue to the nerves may alleviate discomfort associated with headaches including migraine headaches, vascular headaches, cluster headaches, and tension headaches upon onset or upon onset of an aura to reduce the intensity of the headache or the presentation of the aura.

The device may be incorporated into a frame that resembles eyeglasses or may be incorporated into a headband, hat or other item worn about the head.

Application of the transcutaneous current of the invention for approximately 2 to 30 minutes each day may be sufficient to greatly reduce the incidence or intensity of migraine headaches in persons utilizing the electrical current exposure device. The device may produce less than 0.1 Gauss of electromagnetic force. Therefore, the non-pulsed low voltage electric current of the claimed device (not EMF or electrical pulses) may provide therapeutic benefit to persons with headaches including migraine headaches, vascular headaches, cluster headaches, and tension headaches upon onset or upon onset of an aura to reduce the intensity of the headache or the presentation of the aura. If the patient senses the onset of a headache or an aura, the claimed device may be used to prevent the onset or decrease the severity of primary headaches including migraines and some secondary headaches.

Calculated Resistance:

Using the example of a 9 volt battery, the power supply voltage reduces the output voltage from 9.0 to 5.7V in the Resistor (Resistance=5.7V÷20 mA=0.285 mW or 285 Ohms). The power calculation of the 9.0 volt version of this device is that power=5.7V×0.020 A=0.114 W or 114 mW.

The single pole, single throw switch in the device allows circuit disconnection. Using a rearrangement of Ohm's Law, the calculated resistance is 285 Ohms. The power of this circuit calculated from the equation:

$$\frac{V_s - V_d}{I} = R$$

is 114 milliwatts. Consistent with standard electrical practices, the limiting resistor and disconnect are wired on the positive side of the circuit to minimize the possibility of electrical shorting of wires to other grounded circuitry. The circuit is constructed using 22 AWG stranded wire rated at 0.92 maximum amps for power transmission.

Inductance:

Inductance is the property of a conductor by which a change in current flowing through it induces or creates a voltage in both the conductor itself (self-inductance) and in any nearby conductors (mutual inductance). The opposing change in current or inductance (L), is calculated using the equation:

$$L = \frac{N^2 \mu A}{l}$$

Where:

μ=core material permeability

N=number of turns the wire coil has

A=core area in meters l=the average coil length in meters

The uninsulated wire coil electrode has 6 turns (3 turns on each side of the electrode shaped similar in shape to a spectacles frame) of solid 18 to 24 gauge wire with a core area of 0.050671 square meters (m$^2$) and length of 0.4572 meter (m).

Magnetic Induction Characteristics:

To test the potential for electromagnetic induction of the device, a scalar Gauss meter was designed, tested and used to measure magnetic flux induced by the power-receiving coil. A linear Hall Effect sensor calibrated at 5.000 mV/G and 17 kHz was used to measure the strength of a magnetic field. The quiescent voltage output of the sensor at B=0 G, $T_A$=25° C. was 2.51 V.

Table 2 shows Scalar Gaussmeter measurement of electromagnetic field produced by device while it is operating at 3.2 volts at a power of 114 milliwatts.

|  | Measurement (Volts DC) | | | Strength of Magnetic Field (Gauss) * | | | |
| --- | --- | --- | --- | --- | --- | --- | --- |
| Device | Left Coil | Center | Right Coil | Left Coil | Center | Right Coil | Ambient Temperature |
| JQ-1 | 2.51 | 2.51 | 2.51 | 0.00 | 0.00 | 0.00 | 22.8° C. |
| MG-1 | 2.51 | 2.51 | 2.51 | 0.00 | 0.00 | 0.00 | 23.9° C. |
| MG-2 | 2.51 | 2.51 | 2.51 | 0.00 | 0.00 | 0.00 | 23.9° C. |

* $B = 1000 \times (V_0 - V_1)/k$, in Gauss

No electromagnetic field was detected at the uninsulated wire coil electrode of the claimed device while it was in operation, using a very sensitive model A1324LUA-T linear Hall effect electromagnetic field sensor manufactured by Allegro MicroSystems features a factory programmed sensitivity of 5.0 mV/G, see Table 3.

Table 3 shows Electromagnetic field detection using Hall effect sensor, model A1324LUA-T manufactured by Allegro MicroSystems.

|  | Minimum | Typical | Maximum | Unit |
| --- | --- | --- | --- | --- |
| Sensitivity | 4.750 | 5.000 | 5.250 | mV/G |
| Sensitivity Temperature Coefficient | 0 | 0.03 | 0 | %/° C. |
| Quiescent Voltage Output (B = 0 G, Ta =25° C.) | 2.425 | 2.500 | 2.575 | V |
| Internal Bandwidth | 0 | 17 | 0 | kHz |
| Operating Ambient Temperature | −40 |  | 150 | ° C. |

Where mV/G = milliVolts/Gauss, %/° C. = percent/degree centigrade, V =Volts, kHz = kiloHertz, ° C. =degrees centigrade Six volt version of device:

The 6 volt power source for this version of the device consists of two 3 volt button batteries of 40 mAh (to 2.0 volts) each of constant current. The claimed electronic device is approximately 3 inch×2 inch×1 inch dimensions and weighs approximately 75 grams. The maximum output voltage is 2.6 volts with a maximum output current of 20 milliamps, with a maximum output power of 54 milliwatts, includes an indicator light that the device is functioning. A patient override control by an on/off switch and an automatic overload trip voltage level. may be incorporated into the device.

Method of Treatment:

The direct electric current produced by the device is believed to transcutaneously stimulate nerve branches in the forehead, such as the supraorbital and supratrochlear nerves, to prevent or reduce the intensity of primary and some secondary headaches such as migraine headaches, vascular headaches, cluster headaches and tension headaches, with or without associated aura. The device may be battery-powered and worn with the uninsulated wire coil electrodes centered frontally on the forehead one coil superior to each eye. The device exposes a small constant voltage direct current transcutaneously in the forehead through the uninsulated wire electrodes.

In one embodiment, an electronic device in accordance with the principles of the invention may produce an output of constant direct electric current, without pulses or spikes, of approximately 3.2 volts of direct current. Such current is approximately 20 mA amperage for a power output of 114 mW using a direct current power supply (battery or transformer), a resistor, a fuse, an on/off switch, an indicator light emitting diode, and an approximately 18 to 24 gauge solid wire electrode with two coils of two or more loops each of uninsulated electrically conductive wire to act as non-invasive transcutaneous electrodes.

The device may be used for between 1 and 30 minutes per day to stimulate forehead nerves with transcutaneous direct current to prevent or reduce the intensity of primary and some secondary headaches such as migraine headaches, vascular headaches, cluster headaches and tension headaches, with or without associated aura.

Optionally, the device may be used for between 3 and 10 minutes per day to stimulate forehead nerves with transcutaneous direct current to prevent or reduce the intensity of primary and some secondary headaches such as migraine headaches, vascular headaches, cluster headaches and tension headaches, with or without associated aura. Using the device may reduce the intensity of or onset of an aura.

In another embodiment, the coils may be composed of conductive wire to apply transcutaneous direct electrical current composed of copper, silver, nickel, gold, platinum, palladium, aluminum, graphite, metal alloys containing aluminum, titanium, copper, silver, gold, iron, and magnesium, wires plated with metals such as silver or gold, or any other biocompatible and electrically conductive materials.

The device may be used for between 1 and 30 minutes per day to non-invasively stimulate the forehead nerves to prevent or reduce the intensity of primary and some secondary headaches such as migraine headaches, vascular headaches, cluster headaches and tension headaches, with or without associated aura. Optionally, the device may be used for between 3 and 10 minutes per day to transcutaneously stimulate the forehead to prevent or reduce the intensity of primary and some secondary headaches such as migraine headaches, vascular headaches, cluster headaches and tension headaches, with or without associated aura. Use of the device may reduce the intensity of or eliminate the onset of an aura.

The device may have one or more electrode coils of uninsulated conductive wire for transcutaneous application of direct electrical current composed of any electrically conductive material that is compatible with human skin.

In another embodiment, the device may have an electrical output to the uninsulated wire coil electrodes of between 2.6 and 8.4 volts as power output to the uninsulated coil electrodes of 54 to 142.5 mW and electromotive force output from the uninsulated wire coil electrodes of less than 0.1 Gauss.

The device may be used for between 1 and 30 minutes per day to stimulate forehead nerves with transcutaneous direct current of constant voltage and current to prevent or reduce the intensity of primary and some secondary headaches such as migraine headaches, vascular headaches, cluster headaches and tension headaches, with or without associated aura. Optionally, the device may be used for between 1 and 30 minutes per day to stimulate forehead nerves with transcutaneous direct electric to prevent or reduce the intensity of primary and some secondary headaches such as migraine headaches, vascular headaches, cluster headaches and tension headaches, with or without associated aura.

In another embodiment, the device may use two electrode pads that contain conductive solutions such as TENS pads in place of the two wire coil electrodes composed of two or more loops of wire to deliver 2.6 to 8.4 as output volts of constant direct electric current applied transcutaneously to stimulate forehead nerves.

The device may be used for between 1 and 30 minutes per day to stimulate forehead nerves with transcutaneous direct current to prevent or reduce the intensity of primary and some secondary headaches such as migraine headaches, vascular headaches, cluster headaches and tension headaches, with or without associated aura.

In another embodiment, the uninsulated wire electrodes consist of up to 6 loops of wire with a core area of approximately 0.050671 m$^2$ and length of approximately 0.4572 meter and the electrical output of the device to the uninsulated wire coil is of constant voltage direct current without voltage pulses or spikes and of constant electric current without pulses or spikes in amperage with an output of electromotive force of less than 0.1 Gauss.

The device may use uninsulated wire coil electrodes that may be centered frontally on the forehead with one uninsulated wire coil electrode superior to each eye in position anterior to the supraorbital and supratrochlear nerves or other conducting nerves that are related to the patient's headache or aura.

In another embodiment, the device may be arranged such that the electrodes may be centered frontally on the forehead one electrode coil superior to each eye, anterior to the two optic nerves or elsewhere externally near another conductive nerve that is related to the patient's primary headache of any type.

The device may cause reduction in the intensity of migraine or other primary headaches such as tension headaches by positioning the wire coil electrodes centered frontally on the forehead with one uninsulated wire coil superior to each eye, anterior to the supraorbital and supratrochlear nerves or external to another conductive nerve that is related to the patient's headache or aura.

The device may be used to prevent or reduce the intensity of primary and some secondary headaches such as migraine headaches, vascular headaches, cluster headaches and tension headaches, with or without associated aura by positioning the electrode coils centered frontally on the forehead with one uninsulated wire coil electrode superior to each eye, anterior to the supraorbital and supratrochlear nerves or external to another conductive nerve that is related to the patient's headache or aura.

The device may be used on a daily basis for 1 to 30 minutes per session to prevent or reduce the intensity of primary and some secondary headaches such as migraine headaches, vascular headaches, cluster headaches and tension headaches, with or without associated aura by centering the uninsulated wire coils frontally on the forehead with one wire coil superior to each eye, anterior to the supraorbital and supratrochlear nerves or other conducting nerve that is related to the patient's headache or aura.

In another embodiment, the device may be a battery powered electronic device that produces a constant direct electric current of approximately 2.5 to 8.5 volts without current or voltage spikes, pulses or EMF fields to prevent or reduce the intensity of primary and some secondary headaches such as migraine headaches, vascular headaches, cluster headaches and tension headaches, with or without associated aura when the uninsulated wire coil electrodes are applied to the forehead.

The device may be capable of reducing the incidence of migraine headaches by an average of 80% or greater when applied to the middle of the forehead once daily for a minimum of 5 minutes per day in patients with chronic headaches with or without aura. The device may be capable of reducing the incidence of migraine headaches by an average of 90% or greater when applied to the middle of the forehead daily for a minimum of 5 minutes per day in patients with chronic headaches with or without.

The device causes no pain even with daily use of the device for prevention or the reduction of the intensity of chronic headaches with or without aura.

The device may include uninsulated wire coil electrodes that may be worn as part of or attached to a headband, cap, tiara or other headwear to correctly position the electrode coils on the forehead.

The device many be used to stimulate nerves other than the supraorbital and supratrochlear nerves by applying the uninsulated wire coil electrodes externally over the nerve(s) and to stimulate the nerve(s) using constant voltage and amperage direct current to reduce the intensity of or eliminate primary or secondary headaches other than migraines.

Figure 11:
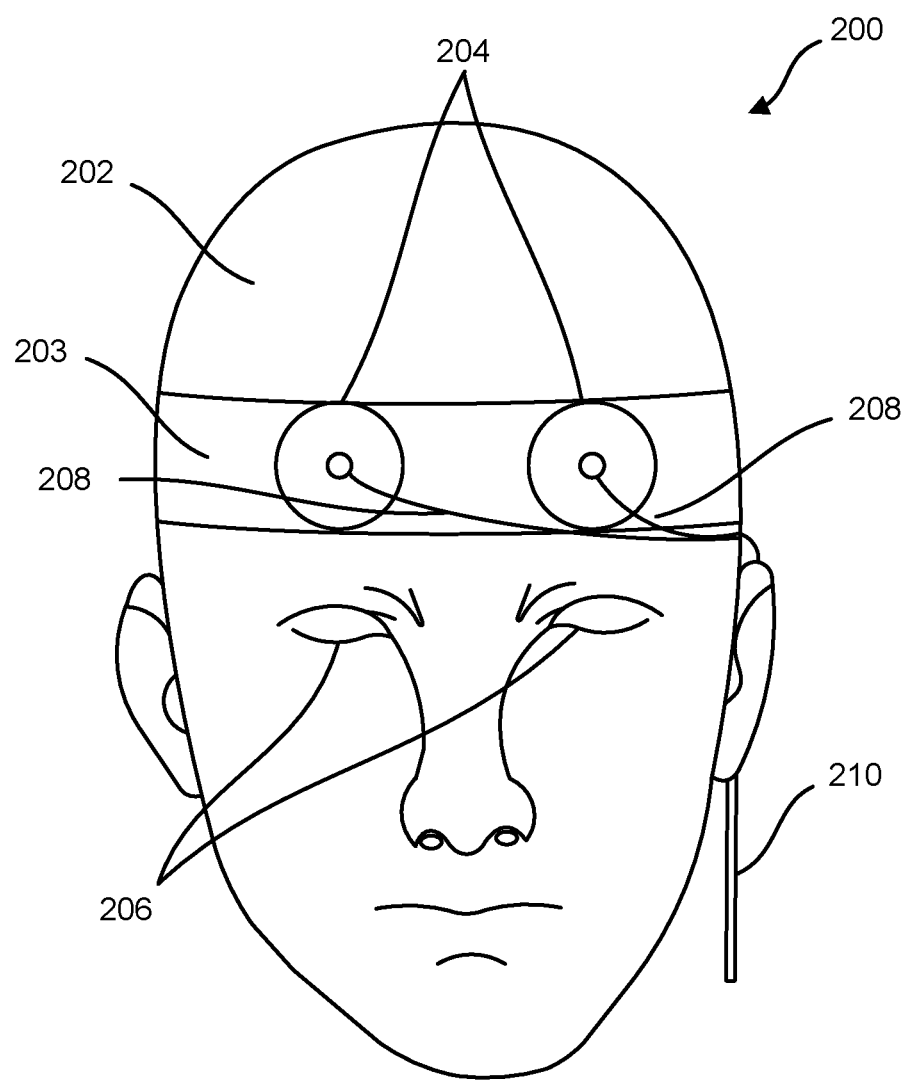
FIG. 11 is a front environmental view of a person wearing an alternative embodiment of a transcutaneous neural stimulation device in accordance with the principles of the invention.

FIG. 11 shows a direct current exposure device 10 that uses transcutaneous electrical nerve stimulation ("TENS") pads in place of exposure coils. In this embodiment, the direct current exposure device is held in place on a user's head 202 by a headband 203. Two TENS pads 204 are placed above each eye 206. Wires 208 are attached to each TENS pad 204 and connect them to conduit 210 which is connected to a power supply similar to those shown above. Each pad 204 may be standard TENS pad or may have an internal coil or an inductor.

Whereas, the present invention has been described in relation to the drawings attached hereto, it should be understood that other and further modifications, apart from those shown or suggested herein, may be made within the spirit and scope of this invention. Descriptions of the embodiments shown in the drawings should not be construed as limiting or defining the ordinary and plain meanings of the terms of the claims unless such is explicitly indicated.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

The invention claimed is:

1. A direct current exposure device comprising:
   an electrical power source having a power supply and a current regulator, the electrical power source configured to generate a direct electrical current having a constant voltage without voltage pulses or spikes in amperage;
   a wire connected to the electrical power source, the wire comprising:
      two uninsulated exposure coils each comprising one or more uninsulated loops of the wire carrying an electric current provided by the electrical power source; and,
      a bridge wire extending between the first exposure coil and the second exposure coil and providing electrical communication between the first exposure coil and the second exposure coil; and,
   a frame supporting the first exposure coil and second exposure coil, the frame being configured to hold the first exposure coil and the second exposure coil on a human forehead above a wearer's eyes:
   wherein the wire is configured to carry the direct electrical current having a constant voltage without voltage pulses or spikes in amperage and the two uninsulated exposure coils are configured to apply a direct current transcutaneously to the forehead.

2. The direct current exposure device of claim 1, wherein the direct electrical current comprises a direct current of approximately 3.2 volts at approximately 20 mA amperage for a power output of 114 mW.

3. The direct current exposure device of claim 1, wherein the two uninsulated exposure coils are configured to carry a current between 2.6 and 8.4 volts and a power output of 54 to 142.5 mW; and, wherein a magnetic field generated by the two uninsulated exposure coils have a flux density of less than 0.1 Gauss.

4. The direct current exposure device of claim 3, wherein the two exposure coils each comprise between 1 and 6 loops of wire and have a core area of approximately 0.050671 $m^2$ and a total length of wire of approximately 0.4572 meters.

5. The direct current exposure device of claim 1, further comprising a support device selected from the group consisting of a headband, cap, tiara or other headwear to position the uninsulated exposure coils on a forehead.

6. The direct current exposure device of claim 1, wherein the uninsulated exposure coils further comprise electrode pads that contain conductive solutions enveloping the uninsulated exposure coils; and wherein the wire is configured to carry between 2.6 and 8.4 volts of constant direct electric current applied transcutaneously.

* * * * *